United States Patent
Altmann et al.

(10) Patent No.: US 11,903,638 B2
(45) Date of Patent: Feb. 20, 2024

(54) REGULATING DELIVERY OF IRREVERSIBLE ELECTROPORATION PULSES ACCORDING TO TRANSFERRED ENERGY

(71) Applicant: BIOSENSE WEBSTER (ISRAEL) LTD., Yokneam (IL)

(72) Inventors: Andres Claudio Altmann, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 319 days.

(21) Appl. No.: 16/710,062

(22) Filed: Dec. 11, 2019

(65) Prior Publication Data

US 2021/0177503 A1    Jun. 17, 2021

(51) Int. Cl.
*A61B 18/12* (2006.01)
*A61B 18/00* (2006.01)
(Continued)

(52) U.S. Cl.
CPC ...... *A61B 18/1492* (2013.01); *A61B 18/1206* (2013.01); *A61B 18/1233* (2013.01);
(Continued)

(58) Field of Classification Search
CPC ............ A61B 18/1492; A61B 18/1206; A61B 2017/00154; A61B 2018/00577;
(Continued)

(56) References Cited

U.S. PATENT DOCUMENTS 5,735,846 A * 4/1998 Panescu ................. A61B 18/00
                                                        606/31
7,001,383 B2 * 2/2006 Keidar ............... A61B 18/1492
                                                        606/41
(Continued)

FOREIGN PATENT DOCUMENTS

CN        103781433 A      5/2014
WO     WO2010068795 A2     6/2010
(Continued)

OTHER PUBLICATIONS

Vivek Y. Reddy, MD et al., "Pulsed Field Ablation for Pulmonary Vein Isolation in Atrial Fibrillation", Journal of the American College of Cardiology, vol. 74, No. 3, 2019.
(Continued)

*Primary Examiner* — Jaymi E Della
*Assistant Examiner* — Abigail M Ziegler
(74) *Attorney, Agent, or Firm* — Dergosits & Noah LLP; Todd A. Noah

(57) ABSTRACT

A medical apparatus includes a probe configured for insertion into a body of a patient and including a plurality of electrodes configured to contact tissue within the body. An electrical signal generator applies bipolar trains of pulses having a voltage amplitude of at least 200 V and having a duration of each of the bipolar pulses less than 20 μs between at least one pair of the electrodes in contact with the tissue, thereby causing irreversible electroporation of the tissue between the at least one pair of the electrodes. One or more electrical sensors sense an energy dissipated between the at least one pair of the electrodes during the trains of the pulses. A controller controls electrical and temporal parameters of the trains of the pulses applied by the electrical signal generator, responsively to the one or more electrical
(Continued)

sensors, so that the dissipated energy satisfies a predefined criterion.

15 Claims, 9 Drawing Sheets

(51) Int. Cl.
*A61B 18/14* (2006.01)
*A61B 34/20* (2016.01)
*A61B 17/00* (2006.01)
*A61B 18/16* (2006.01)

(52) U.S. Cl.
CPC .............. *A61B 2017/00154* (2013.01); *A61B 2017/00199* (2013.01); *A61B 2018/0072* (2013.01); *A61B 2018/00351* (2013.01); *A61B 2018/00363* (2013.01); *A61B 2018/00577* (2013.01); *A61B 2018/00613* (2013.01); *A61B 2018/00636* (2013.01); *A61B 2018/00767* (2013.01); *A61B 2018/00821* (2013.01); *A61B 2018/00827* (2013.01); *A61B 2018/00839* (2013.01); *A61B 2018/00892* (2013.01); *A61B 2018/126* (2013.01); *A61B 2018/1467* (2013.01); *A61B 2018/167* (2013.01); *A61B 2034/2051* (2016.02)

(58) Field of Classification Search
CPC .... A61B 2018/00613; A61B 2018/126; A61B 2018/1467; A61B 2018/00636
See application file for complete search history.

(56) References Cited

U.S. PATENT DOCUMENTS

| | | | |
|---|---|---|---|
| 8,048,067 | B2 | 11/2011 | Davalos |
| 8,221,411 | B2 | 7/2012 | Francischelli |
| 8,562,588 | B2 | 10/2013 | Hobbs |
| 8,620,423 | B2 | 12/2013 | Demarais |
| 8,926,606 | B2 | 1/2015 | Davalos |
| 10,271,893 | B2 | 4/2019 | Stewart |
| 10,342,598 | B2 | 7/2019 | Long |
| 10,531,914 | B2 | 1/2020 | Stewart |
| 2007/0129716 | A1* | 6/2007 | Daw .................. A61B 18/1402 606/34 |
| 2012/0016359 | A1* | 1/2012 | Podhajsky ......... A61B 18/1233 606/34 |
| 2013/0030430 | A1 | 1/2013 | Stewart et al. |
| 2016/0051324 | A1 | 2/2016 | Stewart |
| 2017/0312420 | A1* | 11/2017 | Harlev .............. A61B 18/1482 |
| 2017/0348049 | A1* | 12/2017 | Vrba .................. A61B 18/1492 |
| 2018/0103991 | A1* | 4/2018 | Linhart ............. A61B 18/1477 |
| 2018/0311497 | A1* | 11/2018 | Viswanathan ..... A61N 1/37247 |
| 2018/0360533 | A1* | 12/2018 | Olson ................... A61B 34/20 |
| 2019/0105098 | A1* | 4/2019 | Powell .............. A61B 18/1485 |
| 2019/0117964 | A1 | 4/2019 | Bahrami et al. |
| 2019/0357971 | A1* | 11/2019 | Adi .................... A61B 18/1485 |
| 2020/0060569 | A1* | 2/2020 | Tegg ...................... A61B 5/063 |
| 2020/0289185 | A1* | 9/2020 | Forsyth ............. A61B 18/1233 |
| 2020/0360079 | A1* | 11/2020 | Harlev .................... G06F 3/048 |
| 2021/0154471 | A1* | 5/2021 | Frick ................... A61N 1/0502 |

FOREIGN PATENT DOCUMENTS

| | | | |
|---|---|---|---|
| WO | 2012147072 | A1 | 11/2012 |
| WO | 2017024123 | A1 | 2/2017 |
| WO | WO-2019157359 | A1 * | 8/2019 ......... A61B 18/1206 |
| WO | 2019173309 | A1 | 9/2019 |
| WO | 2019185331 | A1 | 10/2019 |

OTHER PUBLICATIONS

Nebojsa Mujovic et al., "Catheter Ablation of Atrial Fibrillation: An Overview for Clinicians", Adv. Ther. 34: 1897-1917, 2017.
World Health Organization Study: Atrial Fibrillation is a Growing Global Health Concern, Dec. 17, 2013.
Office Action from corresponding Chinese Patent Application No. 202010078836.9, dated Dec. 15, 2020.
International Search Report and Written Opinion from corresponding International Patent Application No. PCT/IB2020/050682, dated Jun. 19, 2020.
Search Report from corresponding Japanese Patent Application No. 2022535606 dated Aug. 18, 2023.

* cited by examiner

REGULATING DELIVERY OF IRREVERSIBLE ELECTROPORATION PULSES ACCORDING TO TRANSFERRED ENERGY

FIELD OF THE INVENTION

The present invention relates generally to medical equipment, and particularly to methods and devices for monitoring the total electrical energy injected in an irreversible electroporation (IRE) procedure.

BACKGROUND

Irreversible electroporation (IRE) is a soft tissue ablation technique that applies short pulses of strong electrical fields to create permanent and hence lethal nanopores in the cell membrane, thus disrupting the cellular homeostasis (internal physical and chemical conditions). Cell death following IRE results from apoptosis (programmed cell death) and not necrosis (cell injury, which results in the destruction of a cell through the action of its own enzymes) as in all other thermal or radiation based ablation techniques. IRE is commonly used in tumor ablation in regions where precision and conservation of the extracellular matrix, blood flow and nerves are of importance.

SUMMARY

Exemplary embodiments of the present invention that are described hereinbelow provide improved methods and devices for performing an IRE procedure.

There is therefore provided, in accordance with an exemplary embodiment of the invention, medical apparatus, including a probe configured for insertion into a body of a patient and including a plurality of electrodes configured to contact tissue within the body. An electrical signal generator is configured to apply bipolar trains of pulses having a voltage amplitude of at least 200 V and having a duration of each of the bipolar pulses less than 20 µs between at least one pair of the electrodes in contact with the tissue, thereby causing irreversible electroporation of the tissue between the at least one pair of the electrodes. One or more electrical sensors are coupled to an output of the electrical signal generator and configured to sense the energy dissipated between the at least one pair of the electrodes during the trains of the pulses. A controller is configured to control electrical and temporal parameters of the trains of the pulses applied by the electrical signal generator, responsively to the one or more electrical sensors, so that the dissipated energy satisfies a predefined criterion.

In one exemplary embodiment, the electrical parameters controlled by the controller include a voltage. Alternatively or additionally, the electrical parameters controlled by the controller include a current.

In some exemplary embodiments, the controller is configured to control the electrical parameters so that the dissipated energy between each pair of the electrodes meets a specified target value. In one exemplary embodiment, the controller is configured to adjust a peak amplitude of the pulses that are applied between the at least one pair of the electrodes so that the dissipated energy satisfies the predefined criterion.

Typically, the one or more electrical sensors are configured to measure a voltage and a current flowing between the at least one pair of the electrodes in a sequence of time intervals, and the controller is configured to measure the dissipated energy by computing a sum of a product of the voltage and the current over the sequence of the time intervals.

In further exemplary embodiments, the controller is configured to control the temporal parameters so that the dissipated energy between each pair of the electrodes meets a specified target value. In one exemplary embodiment, the controller is configured to adjust a number of the pulses that are applied between the at least one pair of the electrodes so that the dissipated energy satisfies the predefined criterion. Alternatively or additionally, the controller is configured to adjust a duration of the pulses that are applied between the at least one pair of the electrodes so that the dissipated energy satisfies the predefined criterion.

There is also provided, in accordance with an exemplary embodiment of the invention, a method for ablating tissue within a body of a patient. The method includes inserting a probe into the body, wherein the probe includes a plurality of electrodes configured to contact the tissue. Bipolar trains of pulses having a voltage amplitude of at least 200 V and having a duration of each of the bipolar pulses less than 20 µs are applied between at least one pair of the electrodes in contact with the tissue, thereby causing irreversible electroporation of the tissue between the at least one pair of the electrodes. the energy dissipated between the at least one pair of the electrodes during the trains of the pulses is measured, and electrical and temporal parameters of the trains of the pulses applied by the electrical signal generator are controlled, responsively to the measured energy, so that the dissipated energy satisfies a predefined criterion.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
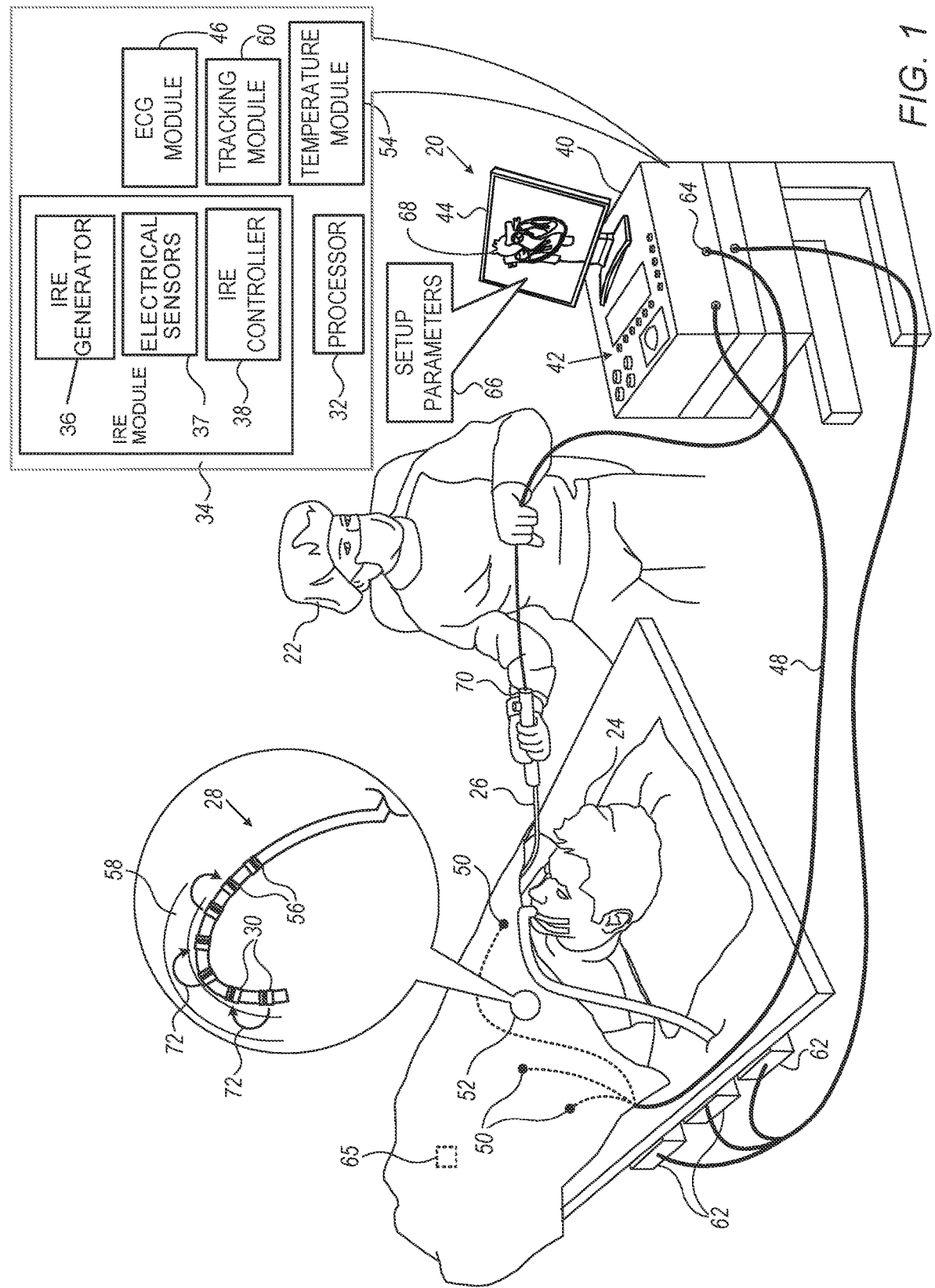
FIG. 1 is a schematic pictorial illustration of a multi-channel IRE system used in an IRE ablation procedure, in accordance with exemplary embodiments of the invention.

IRE is a predominantly non-thermal process, which causes an increase of the tissue temperature by, at most, a few degrees for a few milliseconds. It thus differs from RF (radio frequency) ablation, which raises the tissue temperature by between 20 and 70° C. and destroys cells through heating. IRE utilizes bipolar pulses, i.e., combinations of positive and negative pulses, in order to avoid muscle contraction from a DC voltage. The pulses are applied, for example, between two bipolar electrodes of a catheter.

In order for the IRE-pulses to generate the required nanopores in tissue, the field strength E of the pulses must exceed a tissue-dependent threshold $E_{th}$. Thus, for example, for heart cells the threshold is approximately 500 V/cm, whereas for bone it is 3000 V/cm. These differences in threshold field strengths enable IRE to be applied selectively to different tissues. In order to achieve the required field strength, the voltage to be applied to a pair of electrodes depends both on the targeted tissue and on the separation between the electrodes. The applied voltages may reach up to 2000 V, which is much higher than the typical voltage of 10-200 V in thermal RF ablation.

A bipolar IRE-pulse comprises a positive and a negative pulse applied between two electrodes with pulse widths of 0.5-5 μs and a separation between the positive and negative pulses of 0.1-5 μs. (Herein the terms "positive" and "negative" refer to an arbitrarily chosen polarity between the two electrodes.) The bipolar pulses are assembled into pulse trains, each train comprising between one and a hundred bipolar pulses, with a pulse-to-pulse period of 1-20 μs. To perform IRE ablation at a given location, between one and a hundred pulse trains are applied between a pair of electrodes at the location, with a spacing between consecutive pulse trains of 0.3-1000 ms. The total energy per channel (electrode-pair) delivered in one IRE ablation is typically less than 60 J, and an ablation may last up to 10 s.

When a multi-electrode catheter is used in an IRE procedure, successive pairs of electrodes may be cycled through during the procedure. Taking as an example a 10-electrode catheter, the electrode pairs may be energized in an adjacent fashion (1-2, 2-3, . . . 9-10) or in an interleaved fashion (1-3, 2-4, . . . 8-10). Energizing, for example, adjacent pairs is done in two stages, first energizing the odd-even electrodes 1-2, 3-4, 5-6, 7-8 and 9-10, and then the even-odd electrodes 2-3, 4-5, 6-7, and 8-9.

Before starting the IRE procedure, the physician sets the parameters of the procedure based on, for example, the volume of the tissue to be ablated, required field strength within the tissue, catheter configuration, and the energy to be delivered during the procedure.

Once the procedure has started, the IRE ablation pulses may, in addition to the desired effect of electroporation itself, also affect the impedance of the tissue and/or the contact impedance between the electrodes and the tissue. For a fixed duration and amplitude of a pulse, a change in any of these impedances will affect the current delivered by the pulse, and thus the energy transferred from each pulse into the tissue. This, in turn, will cause the total energy dissipated in the tissue during the procedure to deviate from the amount of energy preset by the physician. Consequently, the effect of the IRE ablation may be different than expected. Moreover, two procedures that have the same energy settings for the IRE ablation may in reality have different amounts of energy transferred to the tissue, thus possibly affecting the repeatability of these kinds of procedures. Specifically, exceeding a preset level of energy may lead to unwanted thermal effects, such as formation of bubbles around the electrodes or charring of the tissue.

The exemplary embodiments of the present invention that are described herein address the problem of controlling the amount of energy that is delivered to the tissue in an IRE procedure by measuring the actual dissipation of energy between the electrodes. Based on this measurement, the pulses delivered by the catheter to the tissue are controlled so that the amount of dissipated energy satisfies a predefined criterion. For example, the criterion may specify that the amount of dissipated energy meets a certain target value (i.e., that the cumulative energy dissipated in each location in the tissue is equal to the target value to within a certain error bound, such as ±5 percent or ±10 percent). Alternatively or additionally, other criteria may be defined.

For these purposes, the exemplary embodiments that are described herein provide a medical apparatus comprising an electrical signal generator and a controller. The medical apparatus further comprises a probe, which is inserted into a body of a patient and which comprises multiple electrodes that contact tissue within the body and are used in applying the electrical signals for the IRE procedure to the tissue. The controller receives setup parameters for implementing an IRE ablation protocol. The parameters may be preset, or they may be adjusted by an operator of the apparatus, such as a physician. The controller transmits to the signal generator instructions to apply trains of bipolar pulses between selected electrodes on the probe. For IRE, these pulses typically have a voltage amplitude of at least 200 V and a duration of each bipolar pulse pair that is less than 20 μs, so as to cause irreversible electroporation of the tissue between the selected electrodes. Alternatively, other suitable pulse parameters may be chosen for this purpose.

To measure the pulse energy that is dissipated in the tissue, electrical sensors are coupled to the outputs of the electrical signal generator. These sensors continuously sense the energy dissipated between the bipolar pairs of electrodes, and convey the measured results to the controller. The controller computes the dissipated energy, and controls the electrical and temporal parameters of the trains of the pulses applied by the electrical signal generator, so that the dissipated energy meets a target value or satisfies some other criterion. The electrical signal generator may be configured either as a voltage source or a current source. In the former case, the electrical parameters controlled by the controller are primarily the voltages of the pulses, whereas in the latter case, the electrical parameters are primarily the currents of the pulses.

To measure the dissipated energy, the controller receives measurements of the voltages between the electrodes, as well as the currents passing through the electrodes, in successive intervals during the ablation procedure. From these measurements the controller estimates the instantaneous power delivered to the tissue, and thus finds the cumulative energy dissipated in the tissue during the IRE procedure. The controller computes possible adjustments required in the trains of the bipolar pulses so that the total energy dissipated in the procedure satisfies the applicable criteria. For this purpose, the controller typically adjusts one or more of the following parameters: pulse amplitude (either voltage amplitude or current amplitude, depending on whether the signal generator is a voltage source or a current source), pulse width (duration), number of pulses per pulse train, and number of pulse trains during the procedure. Alternatively or additionally, the controller may compute adjustments for individual bipolar pulses or pulse trains so that individual pulses or pulse trains will dissipate a preset amount of energy in the tissue.

In some exemplary embodiments, the electrical signal generator used for the IRE procedure is capable of applying, in addition to bipolar pulses for IRE ablation, radio-frequency (RF) signals for thermal RF ablation of the tissue. The measurement of energy dissipation by the electrical sensors can also be used in monitoring and controller the thermal RF ablation process.

IRE Ablation System and IRE Pulses #

FIG. 1 is a schematic pictorial illustration of a multi-channel IRE system 20 used in an IRE ablation procedure, in accordance with exemplary embodiments of the present invention. In the following description, the IRE ablation procedure will also be referred to as "IRE ablation" or "IRE procedure." In the illustrated exemplary embodiment, a physician 22 is performing a multi-channel IRE ablation procedure using IRE system 20. Physician 22 is performing the procedure on a subject 24, using an ablation catheter 26 whose distal end 28 comprises multiple ablation electrodes 30 arrayed along the length of the catheter 26.

IRE system 20 comprises a processor 32 and an IRE module 34, wherein the IRE module comprises an IRE generator 36, electrical sensors 37 and an IRE controller 38. As will be further detailed below, IRE generator 36 generates trains of electrical pulses, which are directed to selected electrodes 30 for performing an IRE procedure. The waveforms (timing and amplitude) of the trains of electrical pulses are controlled by IRE controller 38. Processor 32, as will also be detailed below, handles the input and output interface between IRE system 20 and physician 22.

Processor 32 and IRE controller 38 each typically comprises a programmable processor, which is programmed in software and/or firmware to carry out the functions that are described herein. Alternatively or additionally, each of them may comprise hard-wired and/or programmable hardware logic circuits, which carry out at least some of these functions. Although processor 32 and IRE controller 38 are shown in the figures, for the sake of simplicity, as separate, monolithic functional blocks, in practice some of these functions may be combined in a single processing and control unit, with suitable interfaces for receiving and outputting the signals that are illustrated in the figures and are described in the text. In some exemplary embodiments, IRE controller 38 resides within IRE module 34, as high-speed control signals are transmitted from the IRE controller to IRE generator 36. However, provided that signals at sufficiently high speeds may be transmitted from processor 32 to IRE generator 36, IRE controller 38 may reside within the processor.

Processor 32 and IRE module 34 typically reside within a console 40. Console 40 comprises input devices 42, such as a keyboard and a mouse. A display screen 44 is located in proximity to (or integral to) console 40. Display screen 44 may optionally comprise a touch screen, thus providing another input device.

IRE system 20 may additionally comprise one or more of the following modules (typically residing within console 40), connected to suitable interfaces and devices in system 20:

An electrocardiogram (ECG) module 46 is coupled through a cable 48 to ECG electrodes 50, which are attached to subject 24. ECG module 46 is configured to measure the electrical activity of a heart 52 of subject 24.

A temperature module 54 is coupled to optional temperature sensors, such as thermocouples 56 located adjacent to each electrode 30 on distal end 28 of catheter 26, and is configured to measure the temperature of adjacent tissue 58.

A tracking module 60 is coupled to one or more electromagnetic position sensors (not shown) in distal end 28. In the presence of an external magnetic field generated by one or more magnetic-field generators 62, the electromagnetic position sensors output signals that vary with the positions of the sensors. Based on these signals, tracking module 60 may ascertain the positions of electrodes 30 in heart 52.

The above modules 46, 54, and 60 typically comprise both analog and digital components, and are configured to receive analog signals and transmit digital signals. Each module may additionally comprise hard-wired and/or programmable hardware logic circuits, which carry out at least some of the functions of the module.

Catheter 26 is coupled to console 40 via an electrical interface 64, such as a port or socket. IRE signals are thus carried to distal end 28 via interface 64. Similarly, signals for tracking the position of distal end 28, and/or signals for tracking the temperature of tissue 58, may be received by processor 32 via interface 64 and applied by IRE controller 38 in controlling the pulses generated by IRE generator 36.

An external electrode 65, or "return patch", may be additionally coupled externally between subject 24, typically on the skin of the subject's torso, and IRE generator 36.

Processor 32 receives from physician 22 (or from other user), prior to and/or during the IRE procedure, setup parameters 66 for the procedure. Using one or more suitable input devices 42, physician 22 sets the parameters of the IRE pulse train, as explained below with reference to FIGS. 2-4 and Table 1. Physician 22 further selects pairs of ablation electrodes 30 for activation (for receiving the IRE pulse trains) and the order in which they are activated.

In setting up the IRE ablation, physician 22 may also choose the mode of synchronization of the burst of IRE pulses with respect to the cycle of heart 52. A first option, which is called a "synchronous mode," is to synchronize the IRE pulse burst to take place during the refractory state of heart 52, when the heart is recharging and will not respond to external electrical pulses. The burst is timed to take place after the QRS-complex of heart 52, wherein the delay is approximately 50 percent of the cycle time of the heart, so that the burst takes place during the T-wave of heart 52, before the P-wave. In order to implement synchronous mode, IRE controller 38 times the burst or bursts of IRE pulses based on ECG signals 414 from ECG module 46, shown in FIG. 5, below.

A second synchronization option is an asynchronous mode, wherein the burst of IRE pulses is launched independently of the timing of heart 52. This option is possible, since the IRE burst, typically of a length of 200 ms, with a maximal length of 500 ms, is felt by the heart as one short pulse, to which the heart does not react. Asynchronous operation of this sort can be useful in simplifying and streamlining the IRE procedure.

In response to receiving setup parameters 66, processor 32 communicates these parameters to IRE controller 38, which commands IRE generator 36 to generate IRE signals in accordance with the setup requested by physician 22. Additionally, processor 32 may display setup parameters 66 on display screen 44.

In some exemplary embodiments, processor 32 displays on display 44, based on signals received from tracking module 60, a relevant image 68 of the subject's anatomy, annotated, for example, to show the current position and orientation of distal end 28. Alternatively or additionally, based on signals received from temperature module 54 and ECG module 46, processor 32 may display on display screen 44 the temperatures of tissue 58 at each electrode 30 and the electrical activity of heart 52.

To begin the procedure, physician 22 inserts catheter 26 into subject 24, and then navigates the catheter, using a control handle 70, to an appropriate site within, or external to, heart 52. Subsequently, physician 22 brings distal end 28 into contact with tissue 58, such as myocardial or epicardial tissue, of heart 52. Next, IRE generator 36 generates multiple IRE signals, as explained below with reference to FIG. 3. The IRE signals are carried through catheter 26, over different respective channels, to pairs of ablation electrodes 30, such that currents 72 generated by the IRE pulses flow between the electrodes of each pair (bipolar ablation), and perform the requested irreversible electroporation on tissue 58.

Figure 2:
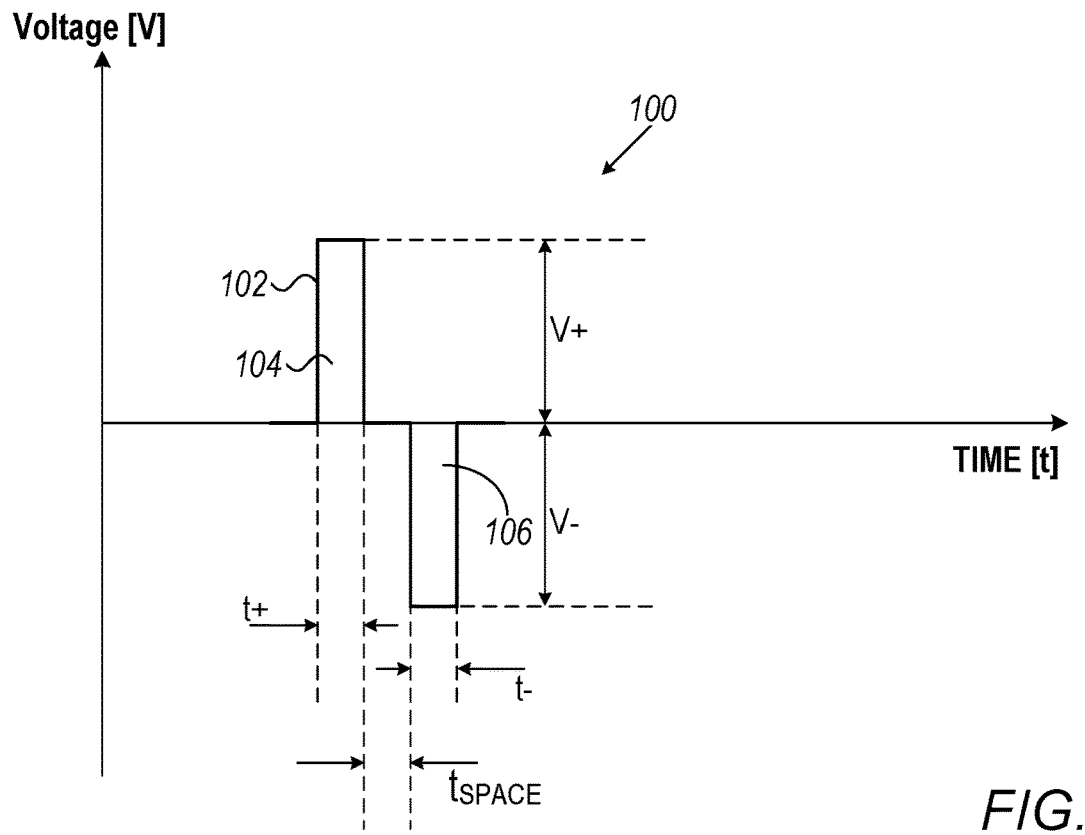
FIG. 2 is a schematic illustration of a bipolar IRE pulse, in accordance with an exemplary embodiment of the invention.

FIG. 2 is a schematic illustration of a bipolar IRE pulse 100, in accordance with an exemplary embodiment of the invention.

A curve 102 depicts the voltage V of bipolar IRE pulse 100 as a function of time t in an IRE ablation procedure. The present exemplary embodiments relate to IRE generator 36, which is configured as a voltage source. Consequently, IRE signals are here described in terms of their voltages. As will be described below, IRE generator 36 may alternatively be configured as a current source, in which case the IRE pulses would be described in terms of their currents. The bipolar IRE pulse comprises a positive pulse 104 and a negative pulse 106, wherein the terms "positive" and "negative" refer to an arbitrarily chosen polarity of the two electrodes 30 between which the bipolar pulse is applied. The amplitude of positive pulse 104 is labeled as V+, and the temporal width of the pulse is labeled as t+. Similarly, the amplitude of negative pulse 106 is labeled as V−, and the temporal width of the pulse is labeled as t−. The temporal width between positive pulse 104 and negative pulse 106 is labeled as $t_{SPACE}$. Typical values for the parameters of bipolar pulse 100 are given in Table 1, below.

Figure 3:
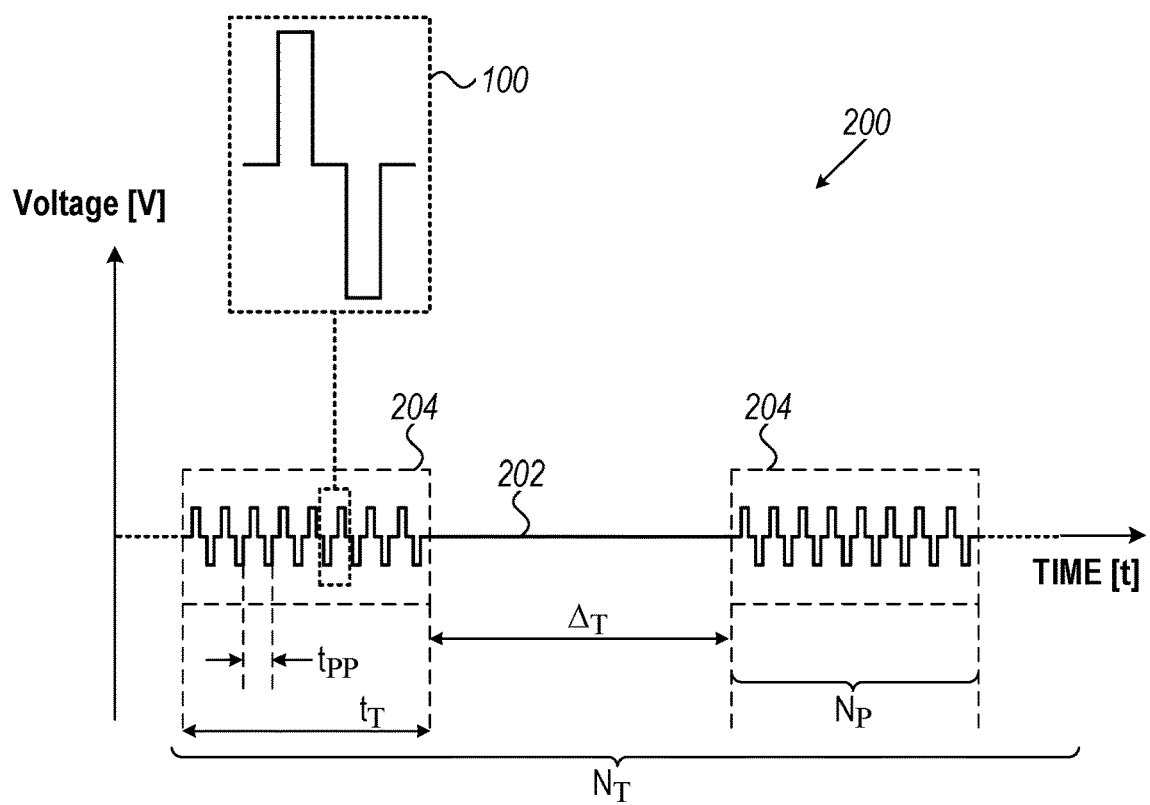
FIG. 3 is a schematic illustration of a burst of bipolar pulses, in accordance with an exemplary embodiment of the invention.

FIG. 3 is a schematic illustration of a burst 200 of bipolar pulses, in accordance with an embodiment of the invention.

In an IRE procedure, the IRE signals are delivered to electrodes 30 as one or more bursts 200, depicted by a curve 202. Burst 200 comprises $N_T$ pulse trains 204, wherein each train comprises $N_p$ bipolar pulses 100. The length of pulse train 204 is labeled as $t_T$. The period of bipolar pulses 100 within a pulse train 204 is labeled as $t_{PP}$, and the interval between consecutive trains is labeled as $\Delta_T$, during which the signals are not applied. Typical values for the parameters of burst 200 are given in Table 1, below.

Figure 4B:
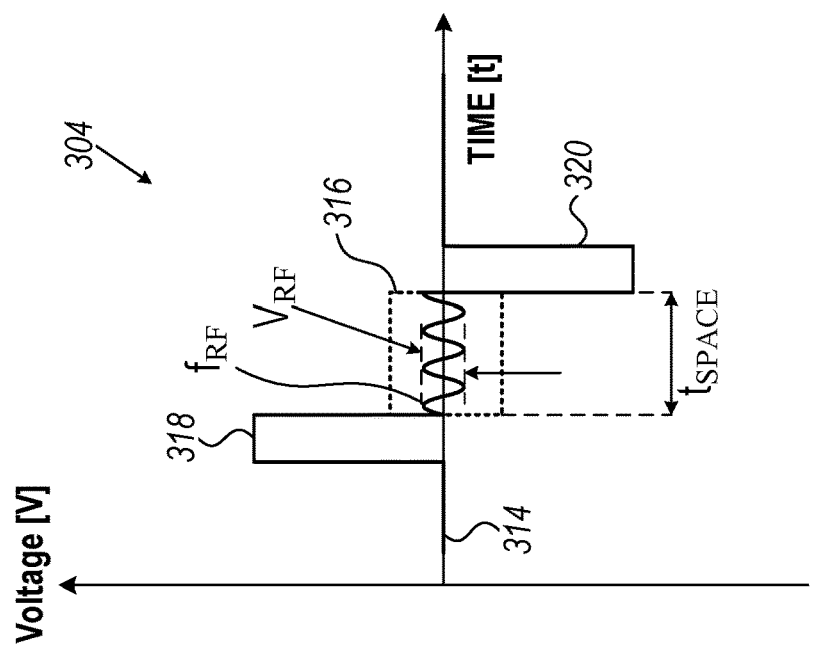
FIGS. 4A-B are schematic illustrations of IRE signals with an incorporated RF signal, in accordance with an exemplary embodiment of the invention.
Figure 4A:
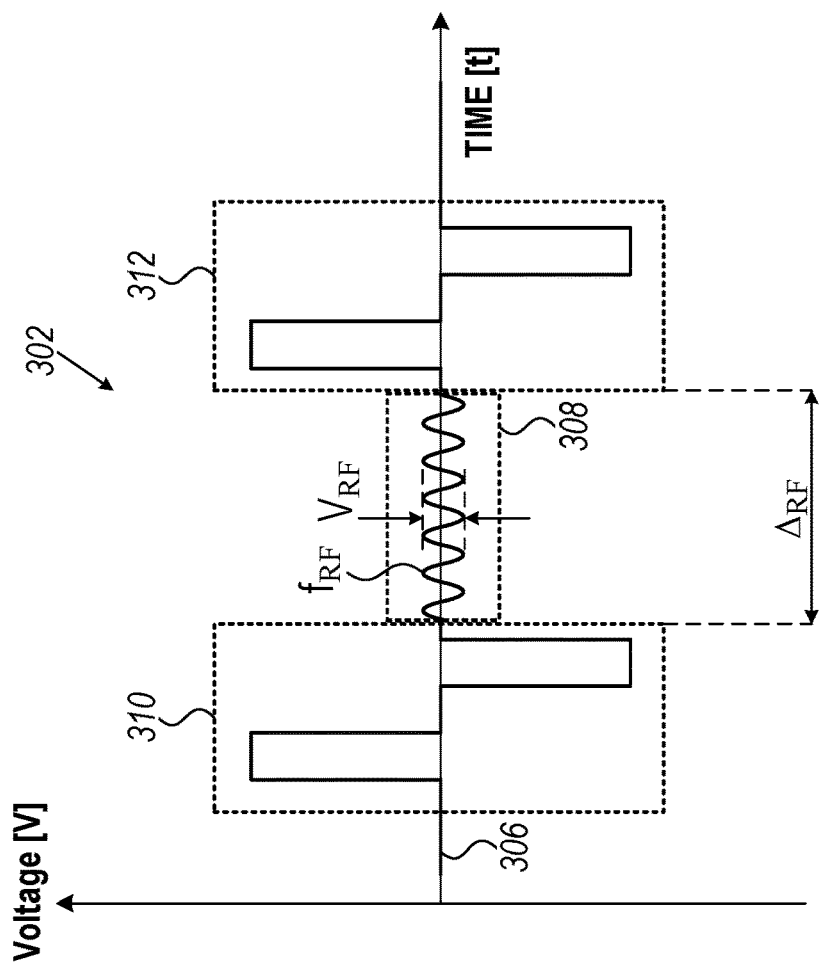

FIGS. 4A-B are schematic illustrations of IRE signals 302 and 304 with an incorporated RF signal, in accordance with exemplary embodiments of the present invention. In the exemplary embodiments shown in FIGS. 4A-B, RF ablation is combined with IRE ablation in order to benefit from both of these ablation modalities.

In FIG. 4A, a curve 306 depicts the voltage V as a function of time t of an RF signal 308 between two bipolar pulses 310 and 312, similar to bipolar pulse 100 of FIG. 2. The amplitude of RF signal 308 is labeled as $V_{RF}$ and its frequency is labeled as $f_{RF}$, and the separation between bipolar pulses 310 and 312 is labeled as $A_{RF}$. Typically the frequency $f_{RF}$ is between 350 and 500 kHz, and the amplitude $V_{RF}$ is between 10 and 200 V, but higher or lower frequencies and amplitudes may alternatively be used.

In FIG. 4B, a curve 314 depicts the voltage V as a function of time t of an RF signal 316 between a positive IRE pulse 318 and a negative IRE pulse 320. IRE pulses 318 and 320 are similar to pulses 104 and 106 of FIG. 2. In this exemplary embodiment, the spacing $t_{SPACE}$ between positive and negative pulses 318 and 320 has been stretched, as indicated in Table 1.

Typical values of the amplitude and frequency of RF signals 308 and 316 are given in Table 1. When an RF signal is inserted into the IRE signal, as depicted either in FIG. 4A or FIG. 4B, the combination of the two signals is repeated to the end of the ablation procedure.

TABLE 1

Typical values for the parameters of IRE signals

| Parameter | Symbol | Typical values |
| --- | --- | --- |
| Pulse amplitudes | V+, V− | 200-2000 V |
| Pulse currents | I | 1-26 A |
| Pulse widths | t+, t− | 0.5-5 μs |
| Spacing between positive and negative pulse | $t_{SPACE}$ | 0.1-5 μs (1-10 ms when an optional RF signal is inserted between the positive and negative pulses) |
| Period of bipolar pulses in a pulse train | $t_{PP}$ | 1-20 μs |
| Length of pulse train | $t_T$ | 100 μs |
| Number of bipolar pulses in a pulse train | $N_P$ | 1-100 |
| Spacing between consecutive pulse trains | $\Delta_T$ | 0.3-1000 ms |
| Number of pulse trains in a burst | $N_T$ | 1-100 |
| Length of a burst | | 0-500 ms |
| Energy per channel | | ≤60 J |
| Total time for IRE signal delivery | | ≤10 s |
| Amplitude of optional RF signal | $V_{RF}$ | 10-200 V |
| Frequency of optional RF signal | $f_{RF}$ | 500 kHz |

IRE Module

Figure 5:
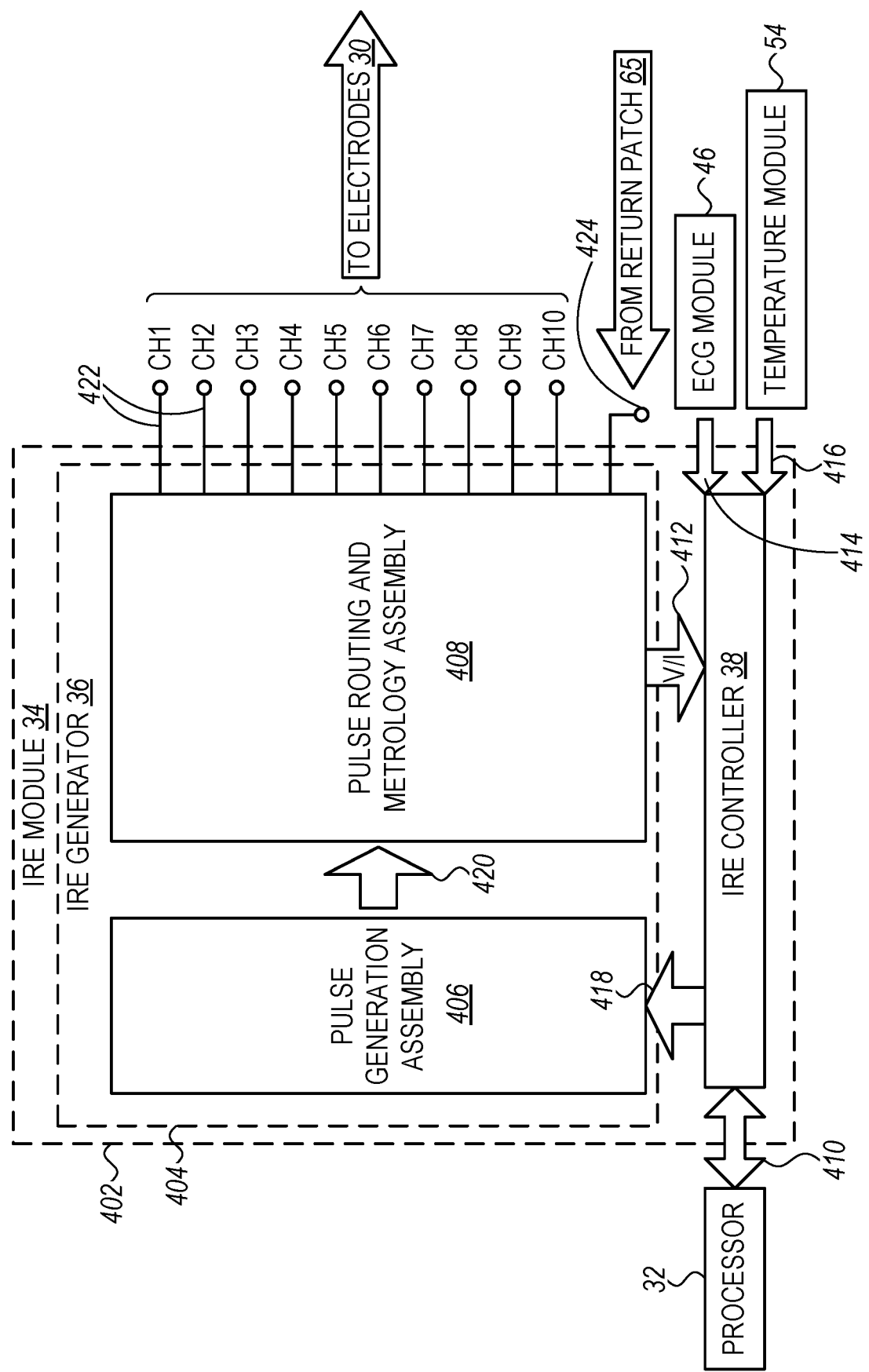
FIG. 5 is a block diagram that schematically illustrates an IRE module and its connections to other modules, in accordance with an exemplary embodiment of the invention.

FIG. 5 is a block diagram that schematically shows details of IRE module 34 and its connections to other modules in system 20, in accordance with an exemplary embodiment of the present invention.

With reference to FIG. 1, IRE module 34 comprises IRE generator 36 and IRE controller 38. IRE module 34 is delineated in FIG. 5 by an outer dotted-line frame 402. Within frame 402, IRE generator 36 is delineated by an inner dotted-line frame 404. IRE generator 36 comprises a pulse generation assembly 406 and a pulse routing and metrology assembly 408, which will both be further detailed in FIGS. 6-9, below.

IRE generator 36 may be configured either as a voltage source or as a current source. Typical voltages of the IRE pulses vary from 200 V to 2000 V, with the ohmic loads for the pulses varying from 75Ω to 200Ω, and consequently the currents varying from 1 A to 26 A. In the present exemplary embodiments, IRE generator 36 is configured as a voltage source. Configuring IRE generator 36 as a current source will be apparent to those skilled in the art after reading the present description.

IRE controller 38 communicates with processor 32 through bi-directional signals 410, wherein the processor communicates to the IRE controller commands reflecting setup parameters 66. IRE controller 38 further receives digital voltage and current signals 412 from pulse routing and metrology assembly 408. The controller utilizes these signals, inter alia, in computing the flow of energy dissipated in tissue 58. Additionally, IRE controller 38 receives digital ECG signals 414 from ECG module 46, and digital temperature signals 416 from temperature module 54, and communicates these signals through bi-directional signals 410 to processor 32.

Figure 10:
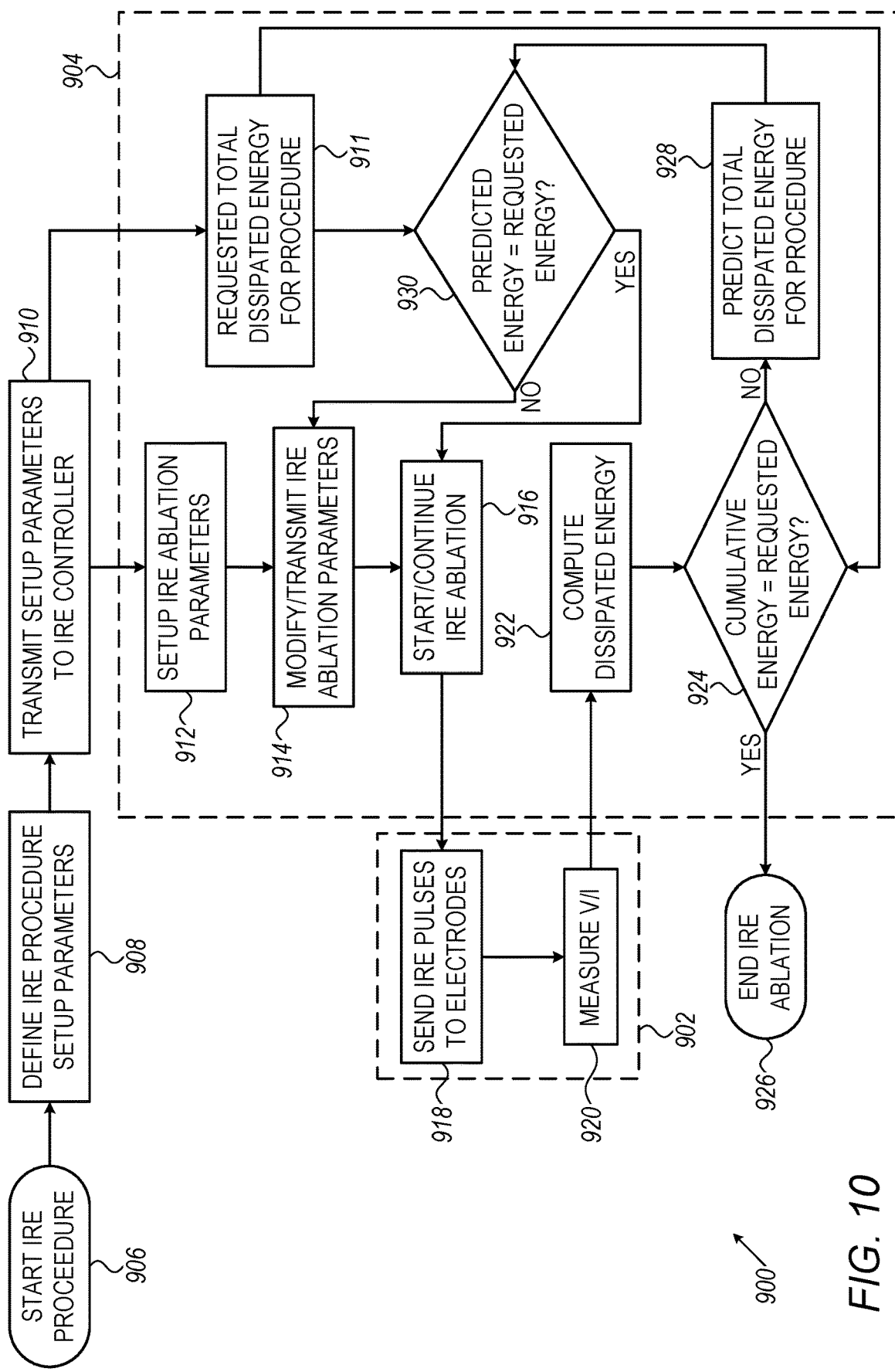
FIG. 10 is a flowchart that schematically illustrates a method for controlling an IRE procedure, in accordance with an exemplary embodiment of the invention.

IRE controller 38 communicates to pulse generation assembly 406 digital command signals 418, derived from setup parameters 66, as well as from the computed dissipation of energy. Command signals 418 cause IRE generator 36 to generate IRE pulses, such as those shown in FIGS. 3-5, while IRE controller 38 adjusts the properties of the IRE pulses based on the computed dissipation of energy and the required dissipated energy. (Further details of the control process are shown in FIG. 10). These IRE pulses are sent to pulse routing and metrology assembly 408 as analog pulse signals 420. Pulse routing and metrology assembly 408 is coupled to electrodes 30 through output channels 422, as well as to return patch 65 through connection 424. FIG. 5 shows ten output channels 422, labelled CH1-CH10. In the following description, a specific electrode is called by the name of the specific channel coupled to it; for example electrode CH5 relates to the electrode that is coupled to CH5 of channels 422. Although FIG. 5 refers to ten channels 422, IRE generator may alternatively comprise a different number of channels, for example 8, 16, or 20 channels, or any other suitable number of channels.

Figure 6:
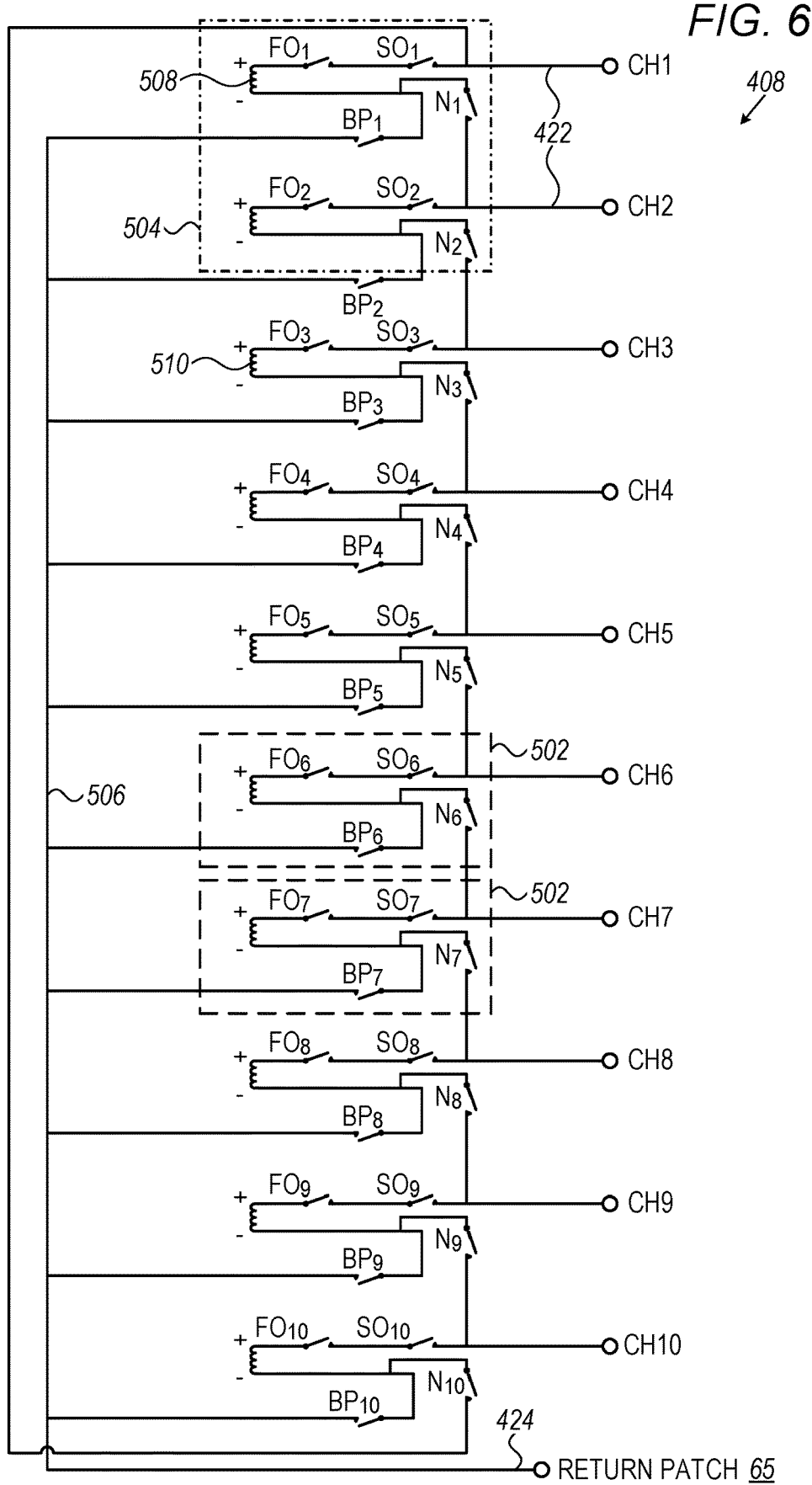
FIG. 6 is an electrical schematic diagram of a pulse routing and metrology assembly in the IRE module of FIG. 5, in accordance with an exemplary embodiment of the illustration.

FIG. 6 is an electrical schematic diagram of pulse routing and metrology assembly 408 of FIG. 5, in accordance with an exemplary embodiment of the invention. For the sake of clarity, the circuits involved in measuring currents and voltages, have been omitted. These circuits will be detailed in FIG. 7, below. Output channels 422 and connection 424 are shown in FIG. 6 using the same labels as in FIG. 5.

Pulse routing and metrology assembly 408 comprises modules 502, with one module for each output channel 422. A pair 504 of adjacent modules 502 is shown in detail in FIG. 7, below.

Each module 502 comprises switches, labelled as $FO_i$, $SO_i$, $N_i$, and $BP_i$ for the $i^{th}$ module. Switches $FO_i$ are all fast switches for switching the IRE ablation from channel to channel, whereas switches $SO_i$, $N_i$, and $BP_i$ are slower relays, used to set up pulse routing and metrology assembly 408 for a given mode of IRE ablation. A typical switching time for fast switches $FO_i$ is shorter than 0.3 μs, whereas slow relays $SO_i$, $N_i$, and $BP_i$ require a switching time of only 3 ms. The examples that are given below demonstrate uses of the switches and relays.

Example 1 demonstrates the use of the switches and relays for IRE ablation between pairs of electrodes according to an odd-even scheme CH1-CH2, CH3-CH4, CH5-CH6, CH7-CH8, and CH9-CH10. (Here the bipolar pulses are applied between each electrode and a first neighbor.) The settings of the switches and relays are shown in Table 2, below.

TABLE 2

Switch and relay settings for Example 1

| Channel $CH_i$ | Fast switch $FO_i$ | Slow relay $SO_i$ | Slow relay $N_i$ | Slow relay BPi |
|---|---|---|---|---|
| CH1 | ON | ON | ON | OFF |
| CH2 | OFF | ON | ON | OFF |
| CH3 | ON | ON | ON | OFF |
| CH4 | OFF | ON | ON | OFF |
| CH5 | ON | ON | ON | OFF |
| CH6 | OFF | ON | ON | OFF |
| CH7 | ON | ON | ON | OFF |
| CH8 | OFF | ON | ON | OFF |
| CH9 | ON | ON | ON | OFF |
| CH10 | OFF | ON | ON | OFF |

Example 2 demonstrates the use of the switches and relays for IRE ablation between pairs of electrodes according to an even-odd scheme CH2-CH3, CH4-CH5, CH6-CH7, and CH8-CH9 (in which the bipolar pulses are applied between each electrode and its second neighbor). For a circular catheter 26, wherein the first and last of electrodes lie side-by-side, the pair CH10-CH1 may be added to the even-odd pairs. The settings of the switches and relays are shown in Table 3, below.

TABLE 3

Switch and relay settings for Example 2

| Channel $CH_i$ | Fast switch $FO_i$ | Slow relay $SO_i$ | Slow relay $N_i$ | Slow relay BPi |
|---|---|---|---|---|
| CH1 | OFF | ON | ON | OFF |
| CH2 | ON | ON | ON | OFF |
| CH3 | OFF | ON | ON | OFF |
| CH4 | ON | ON | ON | OFF |
| CH5 | OFF | ON | ON | OFF |
| CH6 | ON | ON | ON | OFF |
| CH7 | OFF | ON | ON | OFF |
| CH8 | ON | ON | ON | OFF |
| CH9 | OFF | ON | ON | OFF |
| CH10 | ON | ON | ON | OFF |

Combining Examples 1 and 2, a fast IRE ablation between all pairs of electrodes 30 may be accomplished by first ablating with the even-odd scheme of Example 1, then switching each fast switch $FO_i$ to an opposite state (from ON to OFF and from OFF to ON), and then ablating with the odd-even scheme of Example 2. As slow relays $SO_i$, $N_i$, and $BP_i$ are not required to switch their states, the switching takes place at the speed of the $FO_i$ switches.

Example 3 demonstrates IRE ablation between non-adjacent electrodes 30, in this example CH1-CH3, CH4-CH6, and CH7-CH9. Such a configuration may be utilized to cause deeper lesions in tissue 58. The settings of the switches and relays are shown in Table 4, below.

TABLE 4

Switch and relay settings for Example 3

| Channel $CH_i$ | Fast switch $FO_i$ | Slow relay $SO_i$ | Slow relay $N_i$ | Slow relay BPi |
|---|---|---|---|---|
| CH1 | ON | ON | ON | OFF |
| CH2 | ON | ON | ON | OFF |
| CH3 | OFF | ON | ON | OFF |
| CH4 | ON | ON | ON | OFF |
| CH5 | ON | ON | ON | OFF |
| CH6 | OFF | ON | ON | OFF |
| CH7 | ON | ON | ON | OFF |

TABLE 4-continued

Switch and relay settings for Example 3

| Channel $CH_i$ | Fast switch $FO_i$ | Slow relay $SO_i$ | Slow relay $N_i$ | Slow relay BPi |
|---|---|---|---|---|
| CH8 | ON | ON | ON | OFF |
| CH9 | OFF | ON | ON | OFF |
| CH10 | OFF | ON | ON | OFF |

Again, other pairs of electrodes may be rapidly chosen by reconfiguring switches $FO_i$.

Example 4 demonstrates an alternative way to perform an ablation between channels CH1 and CH3. In this example, a BP line 506 is utilized to close the ablation circuit. The settings of the switches and relays are shown in Table 5, below.

TABLE 5

Switch and relay settings for Example 4

| Channel $CH_i$ | Fast switch $FO_i$ | Slow relay $SO_i$ | Slow relay $N_i$ | Slow relay BPi |
|---|---|---|---|---|
| CH1 | ON | ON | OFF | ON |
| CH2 | OFF | ON | OFF | OFF |
| CH3 | ON | ON | OFF | ON |
| CH4 | OFF | ON | OFF | OFF |
| CH5 | ON | ON | OFF | OFF |
| CH6 | OFF | ON | OFF | OFF |
| CH7 | ON | ON | OFF | OFF |
| CH8 | OFF | ON | OFF | OFF |
| CH9 | ON | ON | OFF | OFF |
| CH10 | OFF | ON | OFF | OFF |

In Example 4, the electrical path in pulse routing and metrology assembly 408 couples transformer secondaries 508 and 510 in series. As the distance between electrodes CH1 and CH3 is double to that between adjacent electrodes (for example CH1 and CH2), the voltage between CH1 and CH3 has to be double the voltage between adjacent electrodes so as to have the same electrical field strength between the respective electrodes. This is accomplished by driving the primaries for these two secondaries in opposite phases. Slow switches $SO_i$ are all left in the ON-state in preparation for the next ablation between another pair of electrodes, for example between CH2 and CH4.

As shown in the above examples, the implementation of pulse routing and metrology assembly 408 using relays and fast switches enables a flexible and fast distribution of IRE pulses to electrodes 30, as well as a flexible re-configuration of the applied IRE pulse amplitudes.

Figure 7:
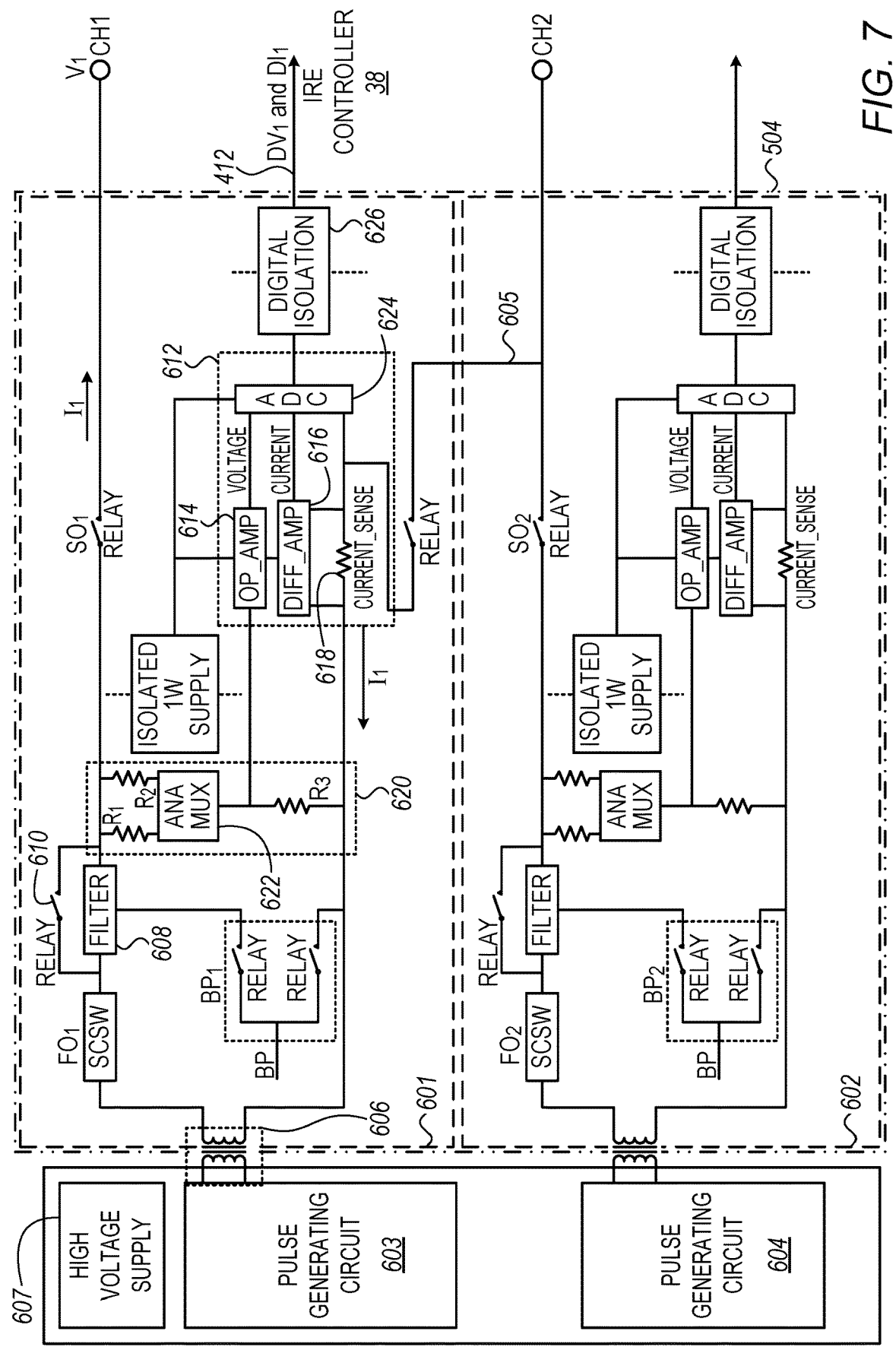
FIG. 7 is an electrical schematic diagram of two adjacent modules in the pulse routing and metrology assembly of FIG. 6, in accordance with an exemplary embodiment of the invention.

FIG. 7 is an electrical schematic diagram of two adjacent modules 601 and 602 of pulse routing and metrology assembly 408, in accordance with an exemplary embodiment of the invention.

Modules 601 and 602 make up pair 504 of FIG. 6, as is shown by dash-dot frame with the same label (504). Modules 601 and 602 are fed by pulse generating circuits 603 and 604, respectively, which comprise, with reference to FIG. 5, parts of pulse generation assembly 406. Modules 601 and 602, in turn, feed channels CH1 and CH2, respectively, similarly to modules 502 of pair 504 in FIG. 6. Two modules 601 and 602 are shown in FIG. 7 in order to show a connection 605 between the modules. As the two modules are identical (and identical to the additional modules in pulse routing and metrology assembly 408), only module 601 is described in detail below.

Figure 8:
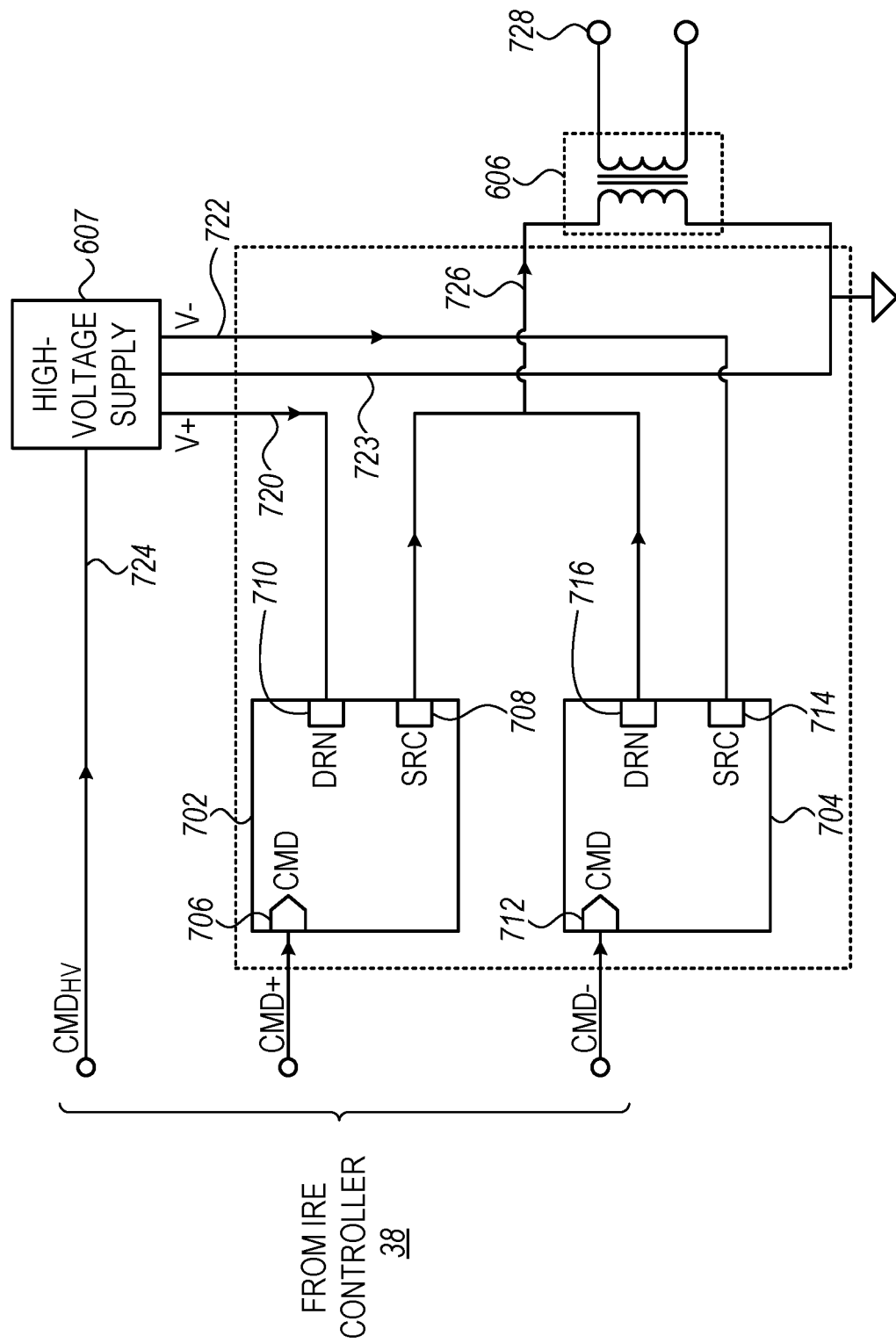
FIG. 8 is an electrical schematic diagram of a pulse generating circuit, a transformer, and a high-voltage supply, in accordance with an exemplary embodiment of the invention.
Figure 9:
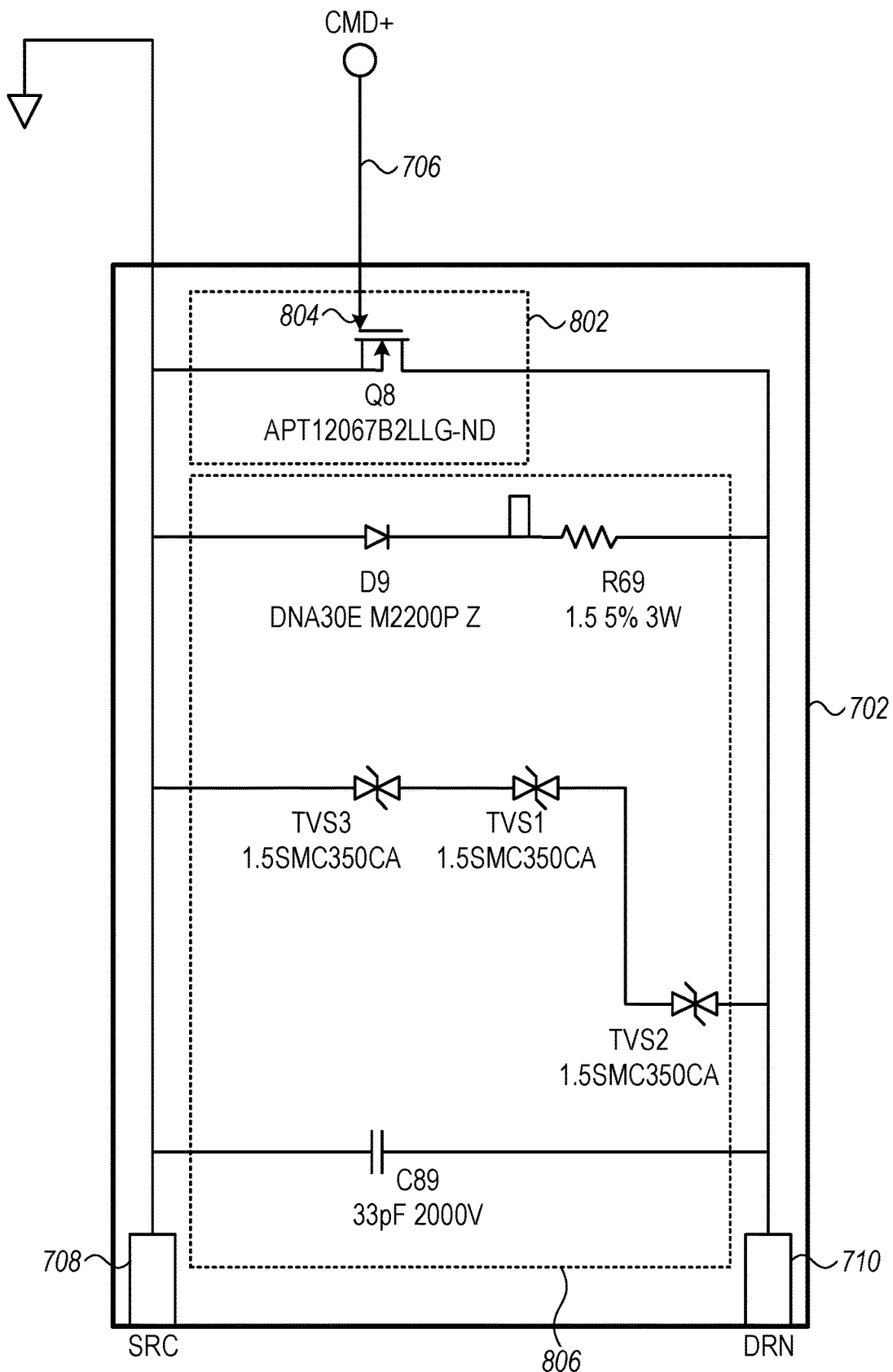
FIG. 9 is an electrical schematic diagram of a switch, in accordance with an exemplary embodiment of the invention.

Further details of pulse generating circuits 603 and 604 are shown in FIGS. 8-9, below. Pulse generation assembly 406 comprises one pulse generating circuit similar to circuits 603 and 604 for each channel of IRE generator 36. Pulse generation assembly 406 further comprises a high-voltage supply 607, detailed in FIG. 8.

Pulse generating circuit 603 is coupled to module 601 by a transformer 606. Fast switch $FO_1$ and slow relays $SO_1$, $N_1$, and $BP_1$ are labelled similarly to FIG. 6. A low-pass filter 608 converts a pulse train transmitted by pulse generating circuit 603 via transformer 606 and switch $FO_1$ to a sinusoidal signal, allowing CH1 to be used for RF ablation. Similarly, each channel of IRE generator 36 may be independently used for RF ablation. The engagement of filter 608 is controlled by a relay 610. An RF signal having a given frequency $f_{RF}$ and amplitude $V_{RF}$ is produced by pulse generating circuit 603 emitting a train of bipolar pulses at the frequency $f_{RF}$ through low-pass filter 608, which converts this pulse train to a sinusoidal signal with the frequency $f_{RF}$. The amplitude of the train of bipolar pulses is adjusted so that the amplitude of the sinusoidal signal is $V_{RF}$.

A voltage $V_1$ and current $I_1$ coupled to CH1 are shown in FIG. 7 as a voltage between channels CH1 and CH2, and a current flowing to CH1 and returning from CH2.

$V_1$ and $I_1$ are measured by a metrology module 612, comprising an operational amplifier 614 for measuring the voltage and a differential amplifier 616 measuring the current across a current sense resistor 618. Voltage $V_1$ is measured from a voltage divider 620, comprising resistors $R_1$, $R_2$, and $R_3$, and an analog multiplexer 622. Analog multiplexer 622 couples in either resistor $R_1$ or $R_2$, so that the voltage dividing ratio of voltage divider 620 is either $R_1/R_3$ or $R_2/R_3$. Metrology module 612 further comprises an analog-to-digital converter (ADC) 624 for converting the measured analog voltage $V_1$ and current $I_1$ to digital signals $DV_1$ and $DI_1$. These digital signals are sent through a digital isolator 626 to IRE controller 38 as signals 412 (FIG. 5). As further detailed in FIG. 10, IRE controller 38 utilizes digital signals $DV_1$ and $DI_1$, as well as the corresponding digital signals from the other modules, to compute the energy dissipated in tissue 58. Digital isolator 626 protects subject 24 (FIG. 1) from unwanted electrical voltages and currents.

Switch $FO_1$, relays $SO_1$, $BP_1$, $N_1$ and 610, and analog multiplexer 622 are driven by IRE controller 38. For the sake of simplicity, the respective control lines are not shown in FIG. 7.

FIG. 8 is an electrical schematic diagram of pulse generating circuit 603, transformer 606, and high-voltage supply 607, in accordance with an exemplary embodiment of the invention.

Pulse generating circuit 603 (FIG. 7) comprises two switches 702 and 704, whose internal details are further shown in FIG. 9, below. Switch 702 comprises a command input 706, a source 708, and a drain 710. Switch 704 comprises a command input 712, a source 714, and a drain 716. Together switches 702 and 704 form a half of an H-bridge (as is known in the art), also called a "half bridge."

High-voltage supply 607 supplies to respective outputs 720 and 722 a positive voltage V+ and a negative voltage V−, adjustable within respective positive and negative ranges of ±(10-2000) V responsively to a signal received by a high-voltage command input 724 from IRE controller 38. High-voltage supply 607 also provides a ground connection 723. A single high-voltage supply 607 is coupled to all pulse generating circuits of pulse generation assembly 406. Alternatively, each pulse generating circuit may be coupled to a separate high-voltage supply.

Drain 710 of switch 702 is coupled to positive voltage output 720, and source 708 of the switch is coupled to an input 726 of transformer 606. When command input 706 receives a command signal CMD+, positive voltage V+ is coupled from positive voltage output 720 to transformer input 726 via switch 702. Source 714 of switch 704 is coupled to negative voltage output 722, and drain 716 of the switch is coupled to transformer input 726. When command input 712 receives a command signal CMD−, negative voltage V− is coupled from negative voltage output 722 to transformer input 726 via switch 704. Thus, by alternately activating the two command signals CMD+ and CMD−, positive and negative pulses, respectively, are coupled to transformer input 726, and then transmitted by transformer 606 to its output 728. The timing of the pulses (their widths and separation) are controlled by command signals CMD+ and CMD−, and the amplitudes of the pulses are controlled by a high-voltage command signal $CMD_{HV}$ to high-voltage command input 724. All three command signals CMD+, CMD−, and $CMD_{HV}$ are received from IRE controller 38, which thus controls the pulses fed into the respective channel of pulse routing and metrology assembly 408.

In an alternative exemplary embodiment (not shown in the figures), a full H-bridge is utilized, with a single-polarity high-voltage supply. This configuration may also be used to produce both positive and negative pulses from the single-polarity source, in response to signals controlling the full H-bridge. An advantage of this exemplary embodiment is that it can use a simpler high-voltage supply, whereas the advantage of a half bridge and a dual high-voltage power supply is that it provides a fixed ground potential, as well as independently adjustable positive and negative voltages.

FIG. 9 is an electrical schematic diagram of switch 702, in accordance with an embodiment of the invention. Switch 704 is implemented in a similar fashion to switch 702.

The switching function of switch 702 is implemented by a field-effect transistor (FET) 802, comprising a gate 804, source 708, and drain 710. Command input 706 is coupled to gate 804, with source 708 and drain 710 coupled as shown in FIG. 8. Additional components 806, comprising Zener diodes, a diode, a resistor, and a capacitor, function as circuit protectors.

FIG. 10 is a flowchart 900 that schematically illustrates a method for controlling an IRE procedure, in accordance with an exemplary embodiment of the present invention. In flowchart 900, a dotted-line frame 902 indicates schematically the steps of the process that take place within IRE generator 36, and a dotted-line frame 904 indicates schematically the steps of the process that take place within IRE controller 38. This particular functional division is described here solely by way of example, however, and the principles of the present method may alternatively be applied in other sorts of IRE module configurations, as well as in other systems for IRE, as will be apparent to those skilled in the art after reading the present description.

The IRE procedure starts in a start step 906. In a setup definition step 908, physician 22 defines, through input devices 42, the setup parameters for the procedure. These setup parameters are based, for example, on the required tissue volume, field strength within the tissue, catheter configuration, and the energy to be delivered into the tissue during the procedure. Processor 32 transmits these setup parameters to IRE controller 38 in a parameter transmission step 910. IRE controller 38 extracts or computes from the setup parameters a requested total dissipated energy in a requested energy step 911. This step defines a target value (for example in Joules) of the energy that is to be dissipated from the IRE pulses into the tissue at each location where ablation is to take place.

In a setup step 912, IRE controller 38 sets up the IRE ablation parameters for IRE generator 36, and transmits them to the generator in a modify/transmit step 914. Once the ablation parameters have been set up in IRE generator 36, IRE controller 38 initiates the ablation by sending an appropriate command to IRE generator 36 in an ablation start/continue step 916. In response to the command, IRE generator 36 applies IRE pulses to electrodes 30 in an IRE pulse step 918. At the same time, metrology module 612 (FIG. 7) within IRE generator 36 measures the voltage $V_i$ and current $I_i$ within each channel i in a V/I measurement step 920, and transmits their values to IRE controller 38.

Based on the received values of $V_i$ and $I_i$, IRE controller 38 computes continuously, in a dissipated energy step 922, the energy dissipated in tissue 58. The computation of the dissipated energy is based on a multiplication of the received values $V_i$ and $I_i$ in each of a sequence of time intervals, and a cumulative summation of the products. In a first comparison step 924, IRE controller 38 checks whether the cumulative dissipated energy from the start of the procedure computed in dissipated energy step 922 is already equal to (or perhaps exceeds) the requested total dissipated energy recorded in requested energy step 911. If the result is affirmative, the IRE ablation is terminated in an end step 926.

When the requested total dissipated energy has not yet been reached at step 924, IRE controller 38 computes, in a prediction step 928, a predicted total dissipated energy assuming the ablation is continued using the current parameters (such as bipolar pulse amplitudes, pulse widths, and number of remaining pulses) of IRE generator 36. In a second comparison step 930, IRE controller 38 compares the predicted total dissipated energy (from step 928) to the requested total dissipated energy (from step 911). When these two are equal, the ablation continues using the current ablation parameters, and the ablation continues through step 916.

When the predicted total dissipated energy deviates from the requested total dissipated energy at step 930, IRE controller 38 modifies the IRE ablation parameters in modify/transmit step 914, and the cycle of FIG. 10 continues. Thus, the feedback provided by the measurement of ablation voltages $V_i$ and currents $I_i$ by metrology module 612 to IRE controller 38 enables the controller to adjust the ablation parameters of IRE generator 36 so as to achieve the requested total dissipated energy for the ablation procedure.

Alternatively or additionally, when the setup parameters specify an energy per pulse or pulse train, the process flow described by flow chart 900 is modified accordingly.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus for regulating delivery of irreversible electroporation (IRE) pulses, the medical apparatus comprising:

a probe configured for insertion into a body of a patient and comprising a plurality of electrodes configured to contact tissue within the body;

an electrical signal generator configured to apply bipolar trains of pulses between at least one pair of the plurality of electrodes, each bipolar pulse having a voltage amplitude of at least 200 V and a duration less than 20 µs between at least one pair of the plurality of electrodes in contact with the tissue, thereby causing IRE of the tissue between the at least one pair of the electrodes;

one or more electrical sensors coupled to an output of the electrical signal generator and configured to measure a voltage and a current flowing between the at least one pair of the plurality of electrodes in a sequence of time intervals; and a controller configured to:
  i) measure a dissipated electrical energy between the at least one pair of the electrodes from the bipolar trains of pulses, which is to be transferred to the tissue during trains of the bipolar trains of pulses, by computing a sum of a product of the voltage and the current flowing between the at least one pair of electrodes over the sequence of the time intervals, the voltage and current being measured by the one or more electrical sensors;
  ii) determine, based on IRE setup parameters, a target value of the dissipated electrical energy to be transferred to the tissue from the bipolar trains of pulses applied to the tissue in contact with the at least one pair of electrodes;
  iii) cause electrical and temporal parameters of the bipolar trains of pulses to be transmitted to the electrical signal generator;
  iv) determine, continuously, whether the measured dissipated electrical energy that is to be transferred to the tissue in contact with the least one pair of electrodes during IRE is equal to or exceeds the target value;
  v) cause the IRE to be terminated when the measured dissipated electrical energy that is transferred to the tissue is equal to or exceeds the target value;
  vi) determine, when the measured dissipated energy that is to be transferred to the tissue is less than the target value, a predicted total dissipated electrical energy to be transferred to the tissue based upon the electrical and temporal parameters;
  vii) compare the predicted total dissipated electrical energy to the target value;
  viii) cause the electrical and temporal parameters to be modified when the predicted total dissipated energy is less than the target value; and
  ix) cause the IRE to be terminated when the measured dissipated electrical energy that is to be transferred to the tissue equals the target value.

2. The medical apparatus according to claim 1, wherein the electrical and temporal parameters comprise a voltage.

3. The medical apparatus according to claim 1, wherein the electrical and temporal parameters comprise a current.

4. The medical apparatus according to claim 1, wherein the controller is configured to adjust a peak amplitude of the bipolar trains of pulses that are applied between the at least one pair of the plurality of electrodes so that the dissipated electrical energy meets the target value.

5. The medical apparatus according to claim 1, wherein the controller is configured to control the electrical and temporal parameters so that the dissipated electrical energy between each pair of the at least one pair of the plurality of electrodes meets the target value.

6. The medical apparatus according to claim 5, and wherein the controller is configured to cause a number of the bipolar trains of pulses that are applied between the at least one pair of the plurality of electrodes to be adjusted so that the dissipated electrical energy meets the target value.

7. The medical apparatus according to claim 5, and wherein the controller is configured to cause the duration of the bipolar trains of pulses that are applied between the at least one pair of the plurality of electrodes to be adjusted so that the dissipated electrical energy meets the target value.

8. A method for ablating tissue within a body of a patient, the method comprising:

inserting a probe into the body, wherein the probe comprises a plurality of electrodes configured to contact the tissue;

providing an electrical signal generator configured to apply bipolar trains of pulses between at least one pair of the plurality of electrodes, each bipolar pulse having a voltage amplitude of at least 200 V and a duration less than 20 µs between at least one pair of the plurality of electrodes in contact with the tissue, thereby causing irreversible electroporation (IRE) of the tissue between the at least one pair of the plurality of electrodes;

determining, based on IRE setup parameters, a target value of dissipated electrical energy to be transferred to the tissue from trains of the bipolar trains of pulses applied to the tissue in contact with the at least one pair of electrodes;

causing electrical and temporal parameters of the trains of the bipolar trains of pulses to be transmitted to the electrical signal generator;

measuring a dissipated electrical energy between the at least one pair of the electrodes from the trains of the bipolar trains of pulses, which is to be transferred to the tissue during the trains of the bipolar trains of pulses, by computing a sum of a product of a voltage and a current flowing between the at least one pair of electrodes over a sequence of time intervals, the voltage and current being measured by one or more electrical sensors coupled to an output of the electrical signal generator;

determining, continuously, whether the measured dissipated electrical energy that is to be transferred to the tissue in contact with the least one pair of electrodes during IRE is equal to or exceeds the target value;

causing the IRE to be terminated when the measured dissipated electrical energy that is to be transferred to the tissue is equal to or exceeds the target value;

determining, when the measured dissipated electrical energy that is to be transferred to the tissue is less than the target value, a predicted total dissipated energy to be transferred to the tissue based upon the electrical and temporal parameters;

comparing the predicted total dissipated electrical energy to the target value;

causing the electrical and temporal parameters to be modified when the predicted total dissipated energy is less than the target value; and causing the IRE to be terminated when the measured dissipated electrical energy that is to be transferred to the tissue equals the target value.

9. The method according to claim 8, wherein the electrical and temporal parameters comprise a voltage.

10. The method according to claim 8, wherein the electrical and temporal parameters comprise a current.

11. The method according to claim 8, wherein modifying the electrical and temporal parameters comprise adjusting a peak amplitude of the bipolar trains of pulses that are applied between the at least one pair of the plurality of electrodes so that the dissipated electrical energy meets the target value.

12. The method according to claim 8, wherein modifying the electrical and temporal parameters comprises setting the temporal parameters so that the dissipated electrical energy between each pair of the at least one pair of the plurality of electrodes meets the target value.

13. The method according to claim 12, wherein modifying the electrical and temporal parameters comprises adjusting a number of the bipolar trains of pulses that are applied between the at least one pair of the plurality of electrodes so that the dissipated electrical energy satisfies the target value.

14. The method according to claim 12, wherein modifying the electrical and temporal parameters comprises adjusting the duration of the bipolar trains of pulses that are applied between the at least one pair of the plurality of electrodes so that the dissipated electrical energy meets the target value.

15. A computer-implemented method for regulating delivery of irreversible electroporation (IRE) pulses during ablation, the method comprising:

determining, based on IRE setup parameters, a target value of dissipated electrical energy to be transferred to tissue within a body of a patient from bipolar trains of pulses applied to the tissue in contact with at least one pair of electrodes of a probe, each bipolar pulse having a voltage amplitude of at least 200 V and a duration less than 20 µs between the at least one pair of electrodes;

causing electrical and temporal parameters of the bipolar trains of pulses to be transmitted to an electrical signal generator;

measuring a dissipated electrical energy between the at least one pair of the electrodes from the bipolar trains of pulses, which is to be transferred to the tissue during the bipolar trains of the pulses, by computing a sum of a product of a voltage and a current flowing between the at least one pair of electrodes over a sequence of time intervals, the voltage and current being measured by one or more electrical sensors coupled to an output of the electrical signal generator;

determining, continuously, whether the measured dissipated electrical energy that is to be transferred to the tissue in contact with the least one pair of electrodes during IRE is equal to or exceeds the target value;

causing the IRE to be terminated when the measured dissipated electrical energy that is to be transferred to the tissue is equal to or exceeds the target value;

determining, when the measured dissipated energy that is to be transferred to the tissue is less than the target value, a predicted total dissipated electrical energy to be transferred to the tissue based upon the electrical and temporal parameters;

comparing the predicted total dissipated electrical energy to the target value;

causing the electrical and temporal parameters to be modified when the predicted total dissipated energy is less than the target value; and causing the IRE to be terminated when the measured dissipated electrical energy that is to be transferred to the tissue equals the target value.

* * * * *